(12) United States Patent
Keady

(10) Patent No.: US 8,142,870 B2
(45) Date of Patent: Mar. 27, 2012

(54) ENERGY RESPONSIVE CONFORMAL DEVICE

(75) Inventor: John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 469 days.

(21) Appl. No.: 12/330,873

(22) Filed: Dec. 9, 2008

(65) Prior Publication Data

US 2009/0155518 A1 Jun. 18, 2009

Related U.S. Application Data

(60) Provisional application No. 61/013,322, filed on Dec. 13, 2007.

(51) Int. Cl.
*B29D 23/00* (2006.01)
*B32B 3/02* (2006.01)

(52) U.S. Cl. ............... 428/36.9; 428/36.91; 428/913; 428/66.4; 428/373; 128/864; 128/865

(58) Field of Classification Search .................. 428/374, 428/373, 913, 212, 36.9, 36.91, 218; 128/864, 128/865
See application file for complete search history.

(56) References Cited

U.S. PATENT DOCUMENTS

| | | | |
|---|---|---|---|
| 4,060,080 A * | 11/1977 | Akiyama | 128/865 |
| 4,732,930 A | 3/1988 | Tanaka | |
| 5,213,580 A | 5/1993 | Slepian | |
| 5,252,318 A | 10/1993 | Joshi | |
| 5,256,765 A | 10/1993 | Leong | |
| 5,333,622 A * | 8/1994 | Casali et al. | 128/864 |
| 5,410,016 A | 4/1995 | Hubbell | |
| 5,514,379 A | 5/1996 | Weissleder | |
| 5,525,334 A | 6/1996 | Ito | |
| 5,575,815 A | 11/1996 | Slepian | |
| 5,589,568 A | 12/1996 | Higashijima | |
| 5,634,946 A | 6/1997 | Slepian | |
| 5,662,609 A | 9/1997 | Slepian | |
| 5,674,287 A | 10/1997 | Slepian | |
| 5,695,480 A | 12/1997 | Evans | |
| 5,702,361 A | 12/1997 | Evans | |
| 5,749,922 A | 5/1998 | Slepian | |
| 5,766,704 A | 6/1998 | Allen | |
| 5,843,156 A | 12/1998 | Slepian | |
| 5,858,746 A | 1/1999 | Hubbell | |
| 5,876,741 A | 3/1999 | Ron | |
| 5,939,485 A | 8/1999 | Bromberg | |
| 5,942,209 A | 8/1999 | Leavitt | |
| 5,976,648 A | 11/1999 | Li | |
| 6,090,911 A | 7/2000 | Petka | |
| 6,113,629 A | 9/2000 | Ken | |
| 6,352,682 B2 | 3/2002 | Leavitt | |
| 6,660,247 B1 | 12/2003 | Gutowska | |
| 6,761,173 B1 * | 7/2004 | Kuno et al. | 128/864 |
| 7,291,389 B1 * | 11/2007 | Bitler et al. | 428/373 |
| 2002/0168319 A1 | 11/2002 | Filler | |

OTHER PUBLICATIONS

Pozrikidis, C. (2009). Fluid Dynamics—Theory, Computation, and Numerical Simulation (2nd Edition), pp. 190.. Springer-Verlag.*

* cited by examiner

*Primary Examiner* — Rena Dye
*Assistant Examiner* — Yan Lan
(74) *Attorney, Agent, or Firm* — RatnerPrestia

(57) ABSTRACT

Sealing devices are presented. The sealing device includes a first material and a second material. The first material responds to energy inputs differently than the second material. The first and second material are operatively connected and configured to be inserted into an orifice.

16 Claims, 5 Drawing Sheets

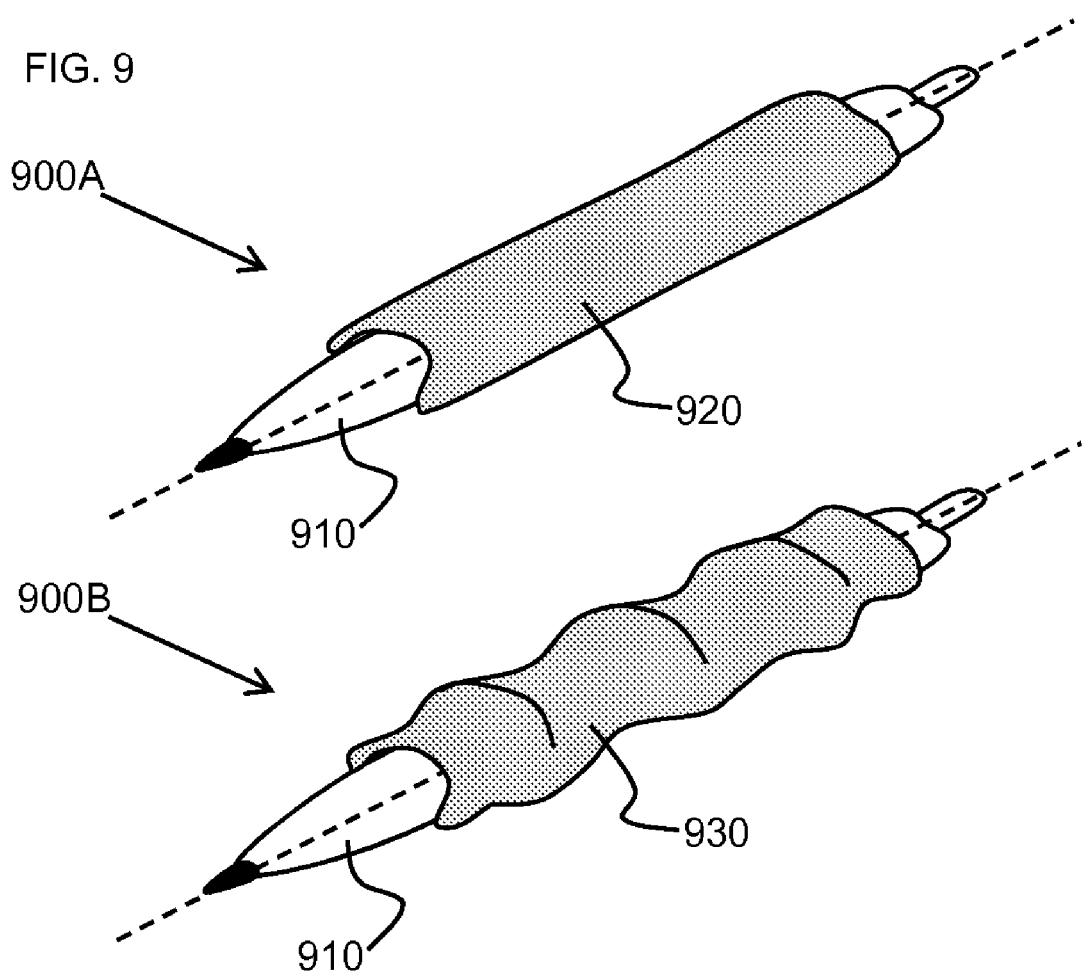

ENERGY RESPONSIVE CONFORMAL DEVICE

CROSS-REFERENCE TO RELATED APPLICATIONS

This application claims the benefit of U.S. provisional patent application No. 61/013,322 filed 13 Dec. 2007. The disclosure of which is incorporated herein by reference in its entirety.

FIELD OF THE INVENTION

The present invention relates to conformal devices and more particularly, though not exclusively, to devices using energy controllable materials.

BACKGROUND OF THE INVENTION

Various devices (e.g. headphones, earbuds, behind the ear, hearing aids, and other devices that direct acoustic energy into an acoustic measuring device (e.g., ear)) have been designed for various uses. Many conventional systems have difficulty sealing in the ear canal. Other orifice (e.g., ear, mouth, anus, nose, artery, vein, pipe, indentation) insertion devices additionally have sealing issues. Additionally devices that have a human interactive piece that have a conformal nature would be useful.

SUMMARY OF THE INVENTION

At least one exemplary embodiment is directed to a sealing device comprising: a first material; and a second material, where the first material responds to energy inputs differently than the second material, and where the first and second material are operatively connected and configured to be inserted into an orifice.

At least one exemplary embodiment is directed to a user interface device comprising: a first material; and a second material, where when the device undergoes a temperature change the first material reacts to the change in temperature more than the second material, where the first and second material are operatively connected and are at least a portion of a user interface.

BRIEF DESCRIPTION OF THE DRAWINGS

Exemplary embodiments of the present invention will become more fully understood from the detailed description and the accompanying drawings, wherein:

FIG. 9 illustrates at least one example of a user interface that conforms to a user's grasp in accordance with at least one exemplary embodiment.

DETAILED DESCRIPTION OF EXEMPLARY EMBODIMENTS OF THE PRESENT INVENTION

Figure 1:
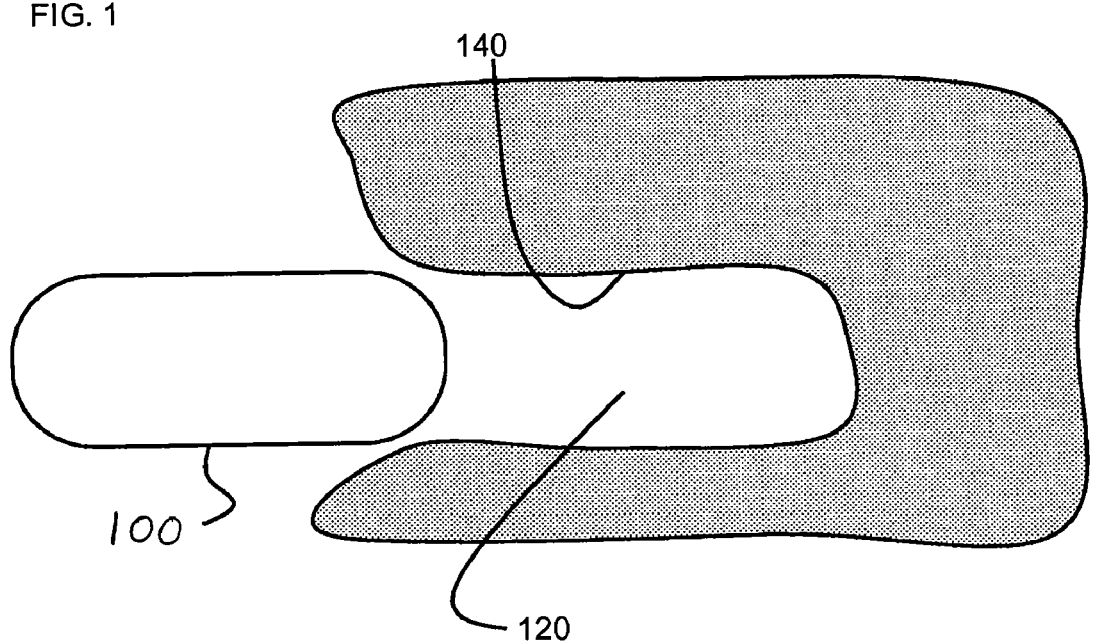
FIG. 1 illustrates a device that is inserted into an orifice.

The following description of exemplary embodiment(s) is merely illustrative in nature and is in no way intended to limit the invention, its application, or uses.

Exemplary embodiments are directed to or can be operatively used on various wired or wireless devices (e.g., earbuds, headphones, ear terminal, behind the ear devices or other acoustic devices as known by one of ordinary skill, and equivalents) or other devices that can be part of a user interface or inserted into an orifice (e.g., ear canal, nose, artery, vein, cavity, recess, anus, throat, pipe, chamber).

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Additionally exemplary embodiments are not limited to ear devices, for example some functionality can be implemented on other systems with speakers and/or microphones for example computer systems, PDAs, Blackberries, cell and mobile phones, and any other device that emits or measures acoustic energy but also for common items such as cups, utensils, medical inserts and devices, and pipe inserts. Additionally, exemplary embodiments can be used with digital and non- digital acoustic systems. Additionally various receivers and microphones can be used, for example MEMs transducers, diaphragm transducers, for example Knowles' FG and EG series transducers.

Notice that similar reference numerals and letters refer to similar items in the following figures, and thus once an item is defined in one figure, it may not be discussed or further defined in the following figures.

Exemplary Embodiments

Non-Limiting Examples and Discussion On Materials:

Some of the materials can be polymers (e.g., viscosity varying polymers), for example polymers that are liquid or less viscous at one temperature then gel or solid at another, or switch between a gel and liquid with PH, current, pressure, or any other variation in energy, or any other similar material as known by one of ordinary skill in the relevant arts. For example the following is a non-limiting list of references that discuss materials that can be used: U.S. Pub. No. 2002/0168319; U.S. Pat. No. 6,660,247; U.S. Pat. No. 6,352,682; U.S. Pat. No. 6,113,629; U.S. Pat. No. 6,090,911; U.S. Pat. No. 5,976,648; U.S. Pat. No. 5,942,209; U.S. Pat. No. 5,939,485; U.S. Pat. No. 5,876,741; U.S. Pat. No. 5,858,746; U.S. Pat. No. 5,843,156; U.S. Pat. No. 5,766,704; U.S. Pat. No. 5,749,922; U.S. Pat. No. 5,702,361; U.S. Pat. No. 5,695,480; U.S. Pat. No. 5,674,287; U.S. Pat. No. 5,662,609; U.S. Pat.

No. 5,634,946; U.S. Pat. No. 5,589,568; U.S. Pat. No. 5,575, 815; U.S. Pat. No. 5,525,334; U.S. Pat. No. 5,514,379; U.S. Pat. No. 5,410,016; U.S. Pat. No. 5,256,765; U.S. Pat. No. 5,252,318; U.S. Pat. No. 5,213,580; U.S. Pat. No. 6,660,247; and U.S. Pat. No. 4,732,930.

Additionally, material referred to herein can also be viscous and can include silicone-based polymers, gels, vinyl elastomers, or any other material of sufficient properties to allow the deformation of a membrane cavity from user contact. Materials can also be used to provide a slow reformation of the original membrane cavity shape after it has been deformed and released. In this regard, a silicone gel or other non-cross-linked polymer or uncatalyzed materials may be used. It should be appreciated that the composition of the fillable material could be altered for applications in which varied membrane characteristics are desired (i.e. more stiffness, durability, more or less deformability and/or longer-lasting deformation). The fillable material can be elastically deformed or it may be deformed by displacement, which is the actual movement or flow of the fillable material in response to pressure, such as that from a user's fingertips. In addition, the fillable material could be altered for applications in which varied temperature or light conditions would be encountered during the use of particular products on which the membrane cavity is mounted. The fillable material can change viscosity in response to energy inputs (e.g., temperature, PH level, vibration, impact, voltage, current).

If a membrane is used, a portion of a membrane connected to a structure (base membrane) can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally, at least a portion of the base membrane can be adhesively attached (e.g., adhesive tape, glue) or mechanically fastened to the support structure.

Note that additional materials that can be used are materials that have a glass transition temperature (Tg) that is close to that of the temperature of the particular energy input. For example if a user grasps a material with a Tg value near the hand temperature the material, which can be glassy, will change to a soft-rubbery or slick material. In monomer or thermoplastic polymers the transition can be to a flowable liquid (note that such a first material can be covered by a membrane that would hold in the flowable material). To make the transition over a temperature range one can use crosslinked polymers.

Note that many of the sizes of the devices can vary so that a device is about 10s of mm in diameters, and 10s mm in length, with a mass varying from 5 grams to hundreds of grams. For example sealing sections can be in the minimal compressed dimension roughly 7 mm (ring diameter), whereas in the uncompressed dimension can be 14 mm (ring diameter). For example at least one exemplary embodiment has a non deformable core diameter of about 5 mm with a length of about 25 mm, with an additional surrounding deformable lay (e.g., sealing section) of an additional 5 mm on either side of the core. The instrument package can be roughly a cylinder of length 10 mm and diameter of about 14 mm.

Note that some of the materials in the device (e.g., outer coating) can be a membrane or multiple membranes and/or layer configuration in accordance with at least one exemplary embodiment. In one configuration an outer membrane contains a fillable material, such as viscosity variable polymers (e.g., that gelify when reaching body temperature) while underneath another membrane encapsulates another medium, which can be a fluid (e.g., liquid, gas) that can be increased or reduced to inflate the inner membrane in the positive/negative radial direction. The medium can be fed via an inflation tube. The device can also include an acoustic channel. Note that although two membranes are mentioned, more can be used with various levels of inflation and various materials, or not inflated and expanded based on temperature or other energy variation methods.

The device can include a sealing section, that can be made of various materials, for example viscosity variable polymers. As the device is inserted into an orifice (e.g., ear, mouth, anus, nose, artery, vein, pipe, recess, cavity) a resistance force can be encountered by a portion of the sealing section. The force can act as an energy variation event which can change the physical properties, for example liquefies (e.g., lowers the viscosity, could still be gel like) the fillable material allowing easy flow or deforms a deformable sealing section. As the impulse forces stop and stability sets in (net equilibrium force reduced) the portion of the sealing section that liquefied in response to a force can then return to its pre-forced state seating the device.

Note that in some materials there is a phase shift in the temporal response of the medium. For example when a force is applied there may be a 10 msec delay in the liquefaction (change in viscosity) of the sealing element's fillable material. Note that materials used can have other thermometric properties.

Note that the device can also be used in consumer goods. For example the device can be a multimaterial wrap around a cup. When the cup heats up a portion of the device can expand, for example forming ridges that keep the person's grip away from the hot cup. Another consumer device example is a pen, where the grip is the device, and as a person holds the pen the material response to the heat of the hand and forms around the grip making the grip form fitted for the user.

Note that although a device is described herein, other devices that can use various viscosity polymers or sealing elements are also meant to fall within the scope of at least one exemplary embodiment of the present invention, for example a drain plug, a pipe plug, a device for sealing the pipe up to a design pressure at which the gel will liquefy and be released or other sealing or impact type situations.

FIG. 1 illustrates a device 110 that is inserted into an orifice 120, which has orifice walls 140. An orifice can be any channel, chamber, recess, cavity, with constraints on content movement in at least two directions. For example a pipe has constraints on contents movement in an up and down direction but not necessarily in an axial direction. Note that a radial direction in this context is considered one direction for a given polar angle, the same radial vector with a different polar angle is a new direction.

Figure 2:
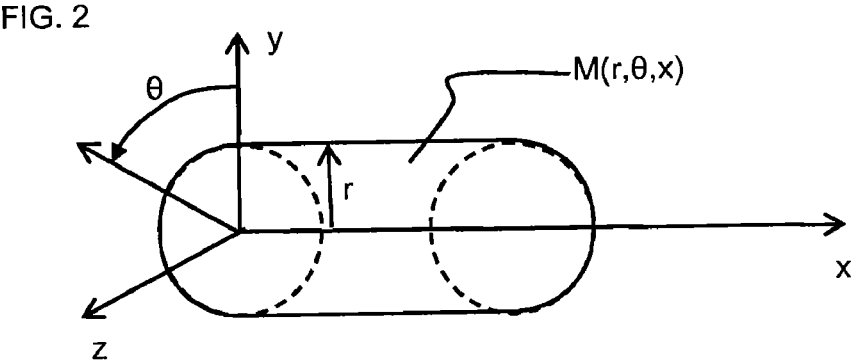
FIG. 2 illustrates an insertable or user interface device arranged in a circumferential direction (θ), a radial direction (r), and/or axially (x direction)

FIG. 2 illustrates an insertable or user interface device arranged in a circumferential direction (θ), a radial direction (r), and/or axially (x direction). Note that material properties (e.g., M(r,θ,x)) of a first material can vary with location (r,θ,x).

Figure 3:
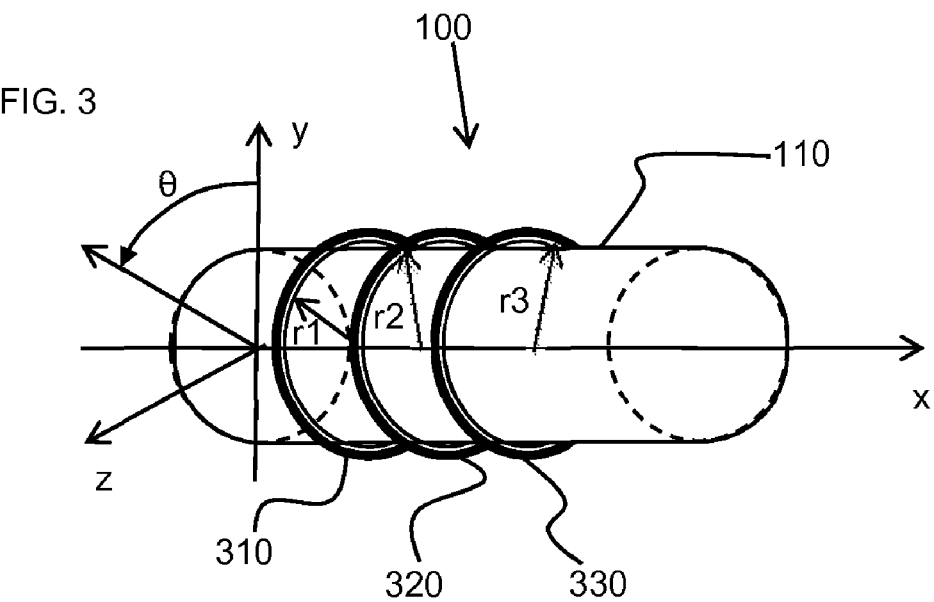
FIG. 3 illustrates a device including a first material circumferentially arranged about a second material, where the first material is separated into multiple sub elements in accordance with at least one exemplary embodiment.

FIG. 3 illustrates a device 100 including a first material circumferentially arranged about a second material 110, where the first material is separated into multiple sub elements (e.g., 310, 320, 330) in accordance with at least one exemplary embodiment. Note that each sub element can have different properties from each other. For example 310 could expand more in a radial direction in response to a temperature change than sub element 320.

Figure 4:
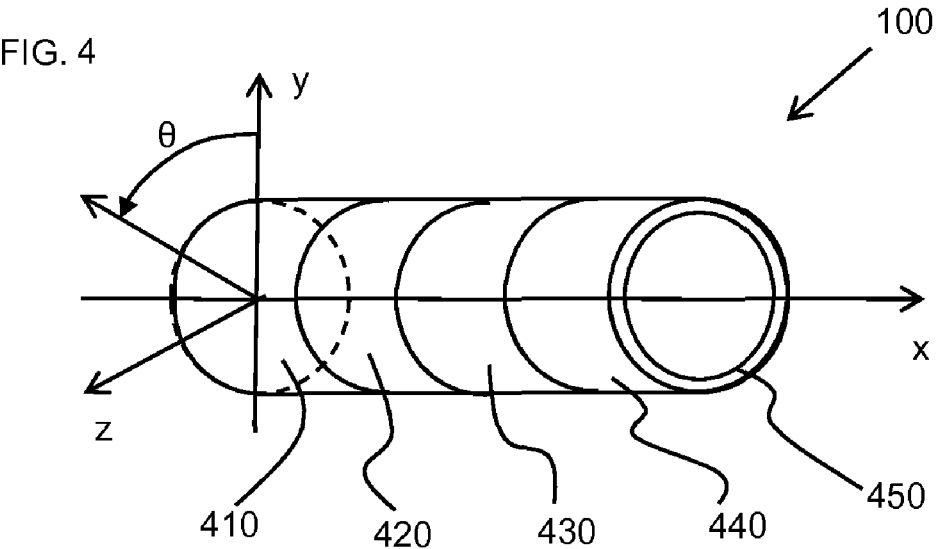
FIG. 4 illustrates a device including a first material which included sub elements arranged axially in accordance with at least one exemplary embodiment.

FIG. 4 illustrates a device 100 including a first material which included sub elements (e.g., 410, 420, 430, and 440) arranged axially (e.g., in the x-direction) about a second material 450 in accordance with at least one exemplary embodiment. Note that each sub element can have different properties from each other. For example 410 could expand more in a radial direction in response to a temperature change than sub element 420. Another example can be that different sub elements have different viscosity variations in response to temperature change.

Figure 5:
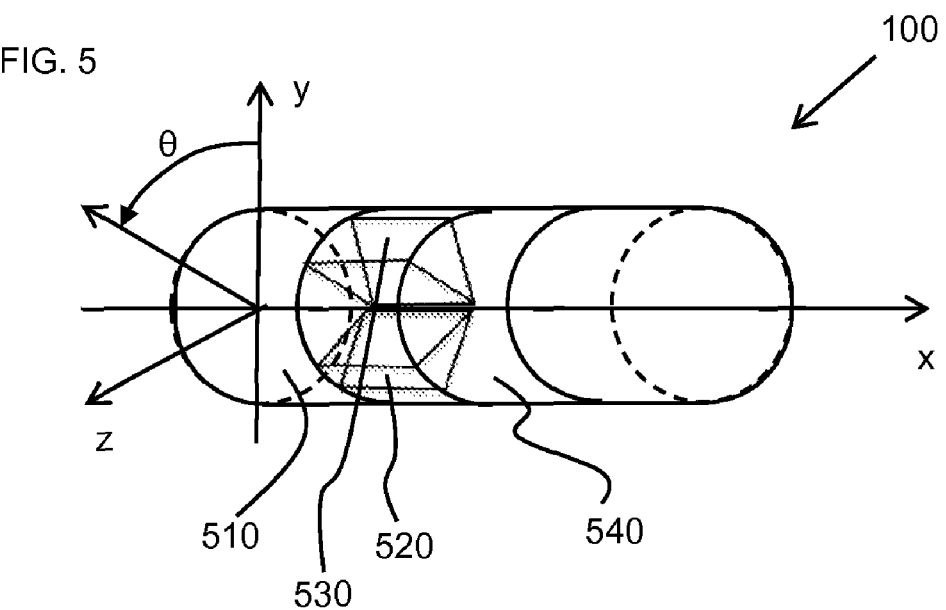
FIG. 5 illustrates a device including a first material which included sub elements arranged circumferentially in accordance with at least one exemplary embodiment.

FIG. 5 illustrates a device 100 including a first material which included sub elements (e.g., 530, 520) arranged circumferentially (e.g., in the θ direction) in accordance with at least one exemplary embodiment in addition to other sub elements (e.g., 510, 540) arranged along an axial direction (e.g., x-direction). Note that at least one exemplary embodiment can have sub elements that vary in the radial direction (e.g., r, see FIG. 7).

Figure 6:
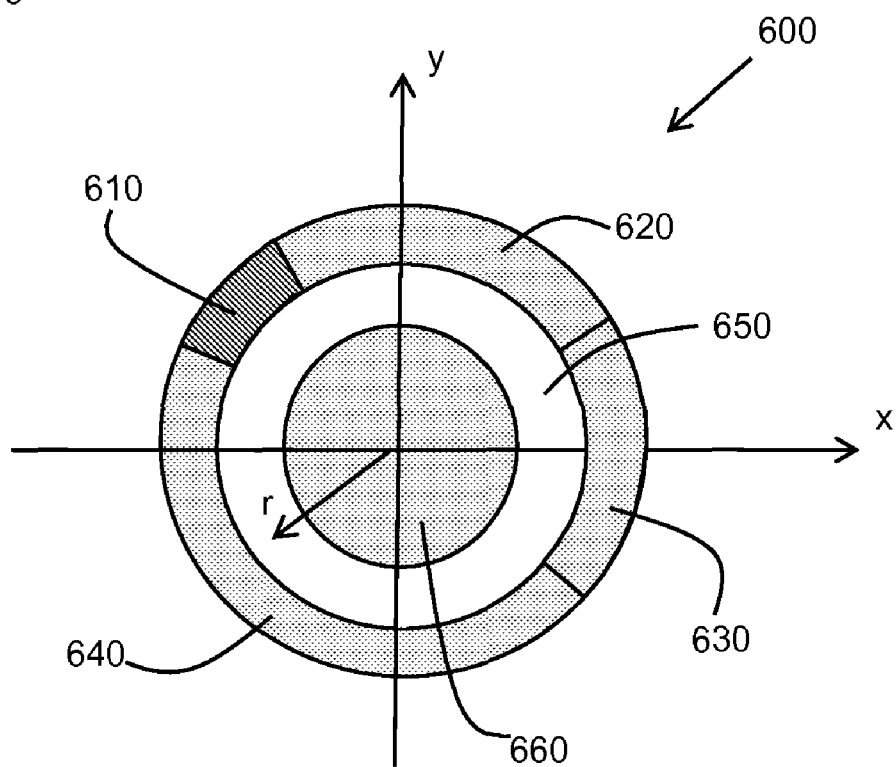
FIG. 6 illustrates a device including at least a first material which included sub elements arranged circumferentially in accordance with at least one exemplary embodiment.

FIG. 6 illustrates a device 600 including at least a first material which included sub elements (e.g., 610, 620, 630, 640, 650, and 660) arranged circumferentially in accordance with at least one exemplary embodiment. Note that the thermometric properties of the sub elements can vary radially as well. For example sub element 610 can expand radially (e.g., r).

Figure 7:
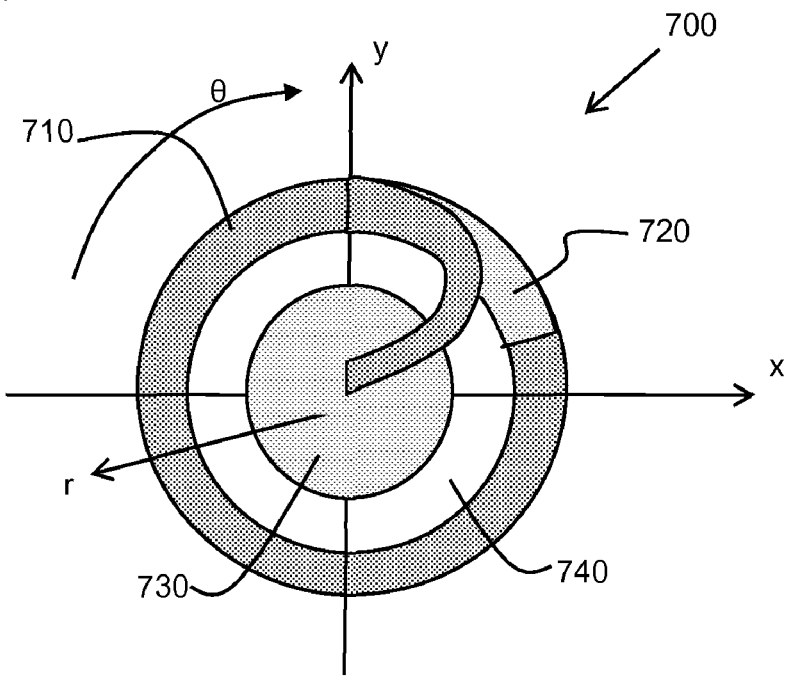
FIG. 7 illustrates a device including at least a first material which included sub elements arranged circumferentially and radially in accordance with at least one exemplary embodiment.

FIG. 7 illustrates a device 700 including at least a first material which included sub elements (e.g., 710, 720, 730, 740) arranged circumferentially (e.g., θ) and radially (e.g., r) in accordance with at least one exemplary embodiment.

Figure 8:
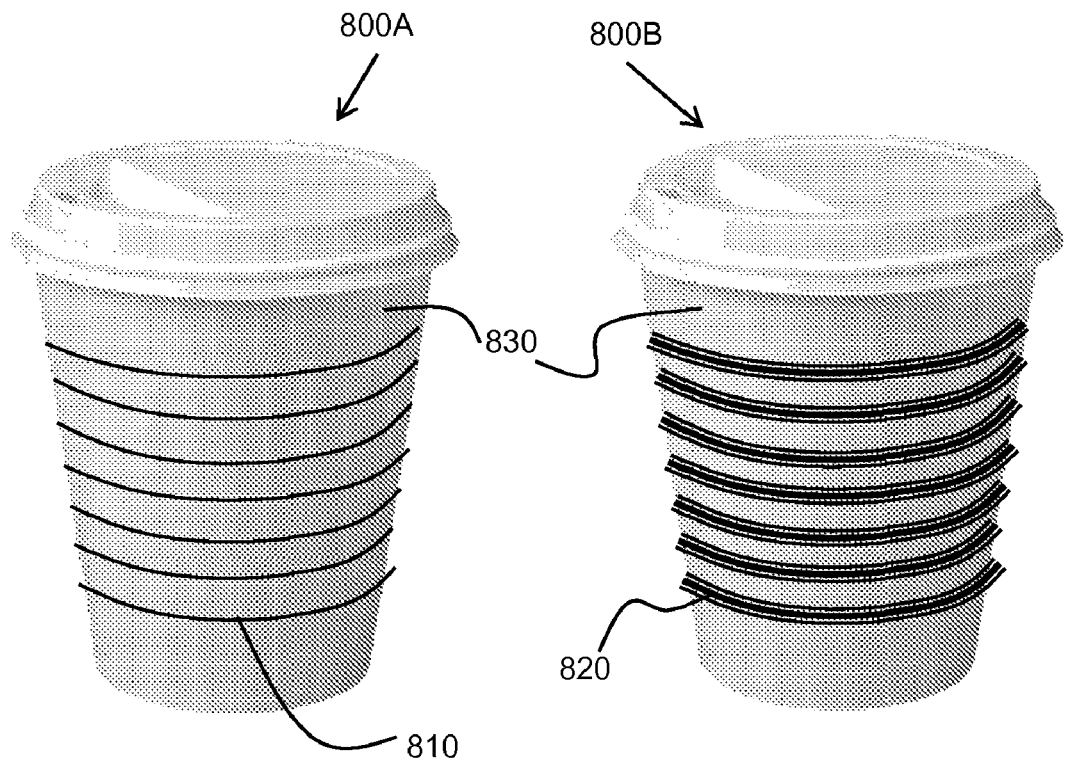
FIG. 8 illustrates at least one example of a container having a first material that varies, for example expands, when energy changes occur, for example a grip that expands keeping a user's hands away from a heated container.

FIG. 8 illustrates at least one example of a container (e.g., 800A and 800B) having a first material (e.g., 810) that varies (e.g., 820) and is attached to a second material (e.g., paper 830), where the first material expands, when energy changes occur. In at least one exemplary embodiment the first material can be a thermal expansive material, for example a grip, that expands when the contents of a container to which the first material is attached, increases. The first material in this non-limiting example can then expand away from the container, keeping a user's fingers from directly contacting the container wall. Likewise such a configuration can be used in devices that have grasps, for example tools, utensils, door handles.

FIG. 9 illustrates at least one example of a user interface (e.g., 900A and 900B) that conforms to a user's grasp in accordance with at least one exemplary embodiment. For example a first material 920 operatively attached (e.g., covering, attached) to a second material 910 (e.g., plastic case), can vary its thermometric property in response to a temperature variation. For example when a user grasps a first material 920, the thermal exchange between a user's grasp and the first material 930 can change the viscosity of the first material so that the first material's viscosity changes so that it flows conforming to the grasp of a user. When the user ungrasps the first material 930 the viscosity of the first material can change again in response to any temperature change in response to a user's lack of grasp. Note that a user's grasp is not needed only as a energy input. For example the property change (e.g., thermometric properties is one property that can be changed) can occur from a temperature change that can occur from feet, head energy loss, or even PH, voltage or current changes.

At least one exemplary embodiment is directed to a sealing device (note that a sealing device can be any device that seals at least a portion of an orifice) comprising: a first material; and a second material, where the first material responds to energy inputs (e.g., temperature and/or temperature changes, pressure and/or pressure changes, voltage and/or voltage changes, current and/or current changes, PH and/or PH changes) differently than the second material (e.g., the thermometric properties of the first material can behave differently than the thermometric properties of the second material, also there can be volume, viscosity, and skin friction changes that are different between the two materials, enthalpy, strength, modulus (e.g., complex, elastic), heat capacity, and hardness, coefficient of thermal expansion), and where the first and second material are operatively connected (e.g., the first material is coated on the second material, or attached physically or with a separation material) and configured to be inserted into an orifice. Note that the device can exert pressure against the walls of the orifice.

In at least one exemplary embodiment the response (e.g., volume increase) of the first material to an energy input (e.g., temperature change), where the expanding (e.g., volume, linear or area increase) of the first material at least partially seals the orifice, for example if the orifice is an ear canal and upon expanding the first material fills more of a cross section of the ear canal than before the energy input.

In at least one exemplary embodiment the energy input can be a temperature change. The temperature change can change the first material so that the first material responds to the temperature change differently than the second material by the first material changing viscosity more than the second material, where the changing of viscosity of the first material conforms a portion of the first material to the inside of an orifice. Note that the portion can be a portion circumferentially, axially, or radially along the orifice.

In at least one exemplary embodiment the operative connection between the first and second materials can be varied, radially, circumferentially, and/or axially, as can the extent of the materials. In essence the first material can vary its location in x, y, z, coordinates, as can the second material.

In at least one exemplary embodiment the first material is separated into at least a first sub element and a second sub element, where the first and second sub elements are arranged perpendicular to the circumferential direction (for example along the axial direction).

In at least one further exemplary embodiment a third material can be operatively attached to a first material. For example the third material can have a particular extent (e.g., in the x,y,z directions, circumferential, axial, and/or radial directions) and the first material can have a different extent (e.g., in the x,y,z directions, circumferential, axial, and/or radial directions).

At least one exemplary embodiment has the first material attached operatively as part of a user interface rather than a device to be inserted into an orifice (for example a first material coating attached to a second material which forms a fork).

In at least one exemplary embodiment the energy input is a temperature change caused by a user grasping the user interface, where when the temperature changes at least a portion of the first material conforms (e.g., the viscosity of the first material changes so that the first material flows or deforms) to the grasp of the user.

In at least one exemplary embodiment the energy input is a temperature change caused by a substance in contact with a container to which the user interface is operatively connected. For example a coffee cup can be filled with hot coffee, the temperature of which conducts through the paper cup (e.g., second material) causing an energy input (e.g., temperature change) to the first material (e.g., a thermally expansive pattern on the cup) so that the first material expands at least in one direction away from the cup, so that a user that grasps the cup will have on average his grasp contact farther from the cup at the elevated temperature than when the cup was at room temperature. Note that other exemplary embodiments include pan handles, pen grips, utensils, chair cushions, arm rests, beds, and other types of user interface systems.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 20 mils) should be interpreted to be "about" the value of the stated number (e.g., about 20 mils).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A sealing device configured to be inserted into an orifice comprising:
    a first material; and
    a body having a second material at least on a portion of an outer surface of the body, the body having first and second ends, the body including a first portion proximate the first end and a second portion proximate the second end,
    wherein the first material is disposed outside of the body on the first portion and on the second material, the first material including plural sub elements,
    a material property of the first material is changed in response to activation by an energy input after being inserted into the orifice, and
    the activation by the energy input causes the first material to conform to the orifice and to seal the orifice in a vicinity of the first portion of the body exclusive of the second portion.

2. The device according to claim 1, where the energy input includes at least one of a temperature change, a current change, a PH change, or a voltage change.

3. The device according to claim 1, where the energy input is a temperature change, where the material property of the first material is changed in response to the temperature change by at least one of a volume, a viscosity, or a skin friction.

4. The device according to claim 1, where the orifice is at least one of an ear canal, an anus, a vein, a nose, a pipe, a recess, and an artery.

5. The device according to claim 1, where the first material is arranged about the body in a circumferential direction of the body.

6. The device according to claim 5, where the material property of the first material changes in a radial direction of the body perpendicular to the circumferential direction.

7. The device according to claim 1, where at least one of the plural sub elements responds differently in response to the activation by the energy input.

8. The device according to claim 1,
    where at least one of the plural sub elements includes an arc segment extending around a portion of a circumference of the body.

9. The device according to claim 1, where a material property of the second material is changed in response to the activation by the energy input.

10. The device according to claim 9, where the material property of the second material is configured to change differently than the material property of the first material in response to the activation by the energy input.

11. The device according to claim 10, where the energy input is a temperature change, where the first material responds to the temperature change differently than the second material by the first material expanding in volume more than the second material, where the expanding of the first material at least partially seals the orifice.

12. The device according to claim 10, where the energy input is a temperature change, where the first material responds to the temperature change differently than the second material by the first material changing a viscosity more than the second material, where the changing of the viscosity of the first material conforms a portion of the first material to the orifice.

13. The device according to claim 1, where the plural sub elements are disposed along an axial direction of the body.

14. The device according to claim 1, where the plural sub elements are configured as annular rings disposed along an axial direction of the body.

15. The device according to claim 1, where the plural sub elements are colocated relative to a radial direction of the body.

16. The device according to claim 1, A sealing device configured to be inserted into an orifice comprising:
    a first material; and
    a body having a second material at least on a portion of an outer surface of the body, the body having first and second ends, the body including a first portion proximate the first end and a second portion proximate the second end,
    wherein the first material is disposed outside of the body on the first portion and on the second material,
    a material property of the first material is changed in response to activation by an energy input after being inserted into the orifice,
    the activation by the energy input causes the first material to conform to the orifice and to seal the orifice in a vicinity of the first portion of the body exclusive of the second portion, and
    where the first material extends helically around the body.

* * * * *